United States Patent [19]
Goodchild et al.

[11] Patent Number: 6,048,848
[45] Date of Patent: Apr. 11, 2000

[54] USE OF PREGNANE-DIONES AS ANALGESIC AGENTS

[75] Inventors: Colin Stanley Goodchild, Glen Waverley; Raymond Nadeson, Prahran, both of Australia

[73] Assignee: Monash University, Clayton, Australia

[21] Appl. No.: 09/026,520

[22] Filed: Feb. 20, 1998

Related U.S. Application Data

[63] Continuation-in-part of application No. PCT/AU96/00531, Aug. 23, 1996, abandoned.

[51] Int. Cl.$^7$ .......................... A01N 45/00; A01N 47/28; A01N 47/34; A61K 31/58
[52] U.S. Cl. .......................... 514/171; 514/177; 514/179; 514/181; 552/586; 552/589
[58] Field of Search .................................... 552/176, 589, 552/586; 514/171, 177, 179, 181

[56] References Cited

U.S. PATENT DOCUMENTS 5,439,900  8/1995  Bukusoglu et al. .................... 514/170

OTHER PUBLICATIONS

Winfree et al., Analgesic effects of 3–alpha–hydroxy–5–alpha–pregnan–20–one, Life Sci., 1992,50(14), 1—7–12.

Parsons et al., Selectivity of Intravenous U– and K–opioids, Br. J. Pharmacol., vol. 98, pp. 544–51.

Primary Examiner—Jose' G. Dees
Assistant Examiner—Alton Pryor
Attorney, Agent, or Firm—Thomas R. Vigil

[57] ABSTRACT

The present invention provides:
the new use of compositions of morphine and compounds of Formula II wherein

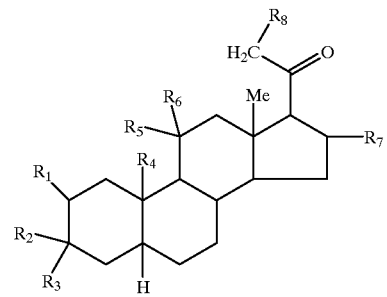

$R^1$ is H or Me, preferably H;
$R^2$ is OH, preferably in alpha conformation;
$R^3$ is H;
or $R^2$ and $R^3$, taken together, are O;
$R^4$ is H or Me, preferably Me and preferably in alpha conformation;
$R^5$ is H;
$R^6$ is H;
or $R^5$ and $R^6$, taken together, are O;
$R^7$ is H or Me, preferably H;
$R^8$=H,OH,OAc,SH,SAc,Cl,Br,F
including solvates thereof, pharmaceutically acceptable derivatives thereof, prodrugs thereof, tautomers thereof, isomers thereof, and metabolites thereof.

8 Claims, 3 Drawing Sheets

FORMULA I

FORMULA II

FORMULA III

FORMULA IV

USE OF PREGNANE-DIONES AS ANALGESIC AGENTS

CROSS REFERENCE TO RELATED APPLICATIONS

This application is a continuation-in-part of PCT Application PCT AU 96/00 531, filed Aug. 23, 1996, now abandoned.

FIELD OF THE INVENTION

This invention relates to compounds and compositions.

In a particular instance, the present invention relates to analgesia, methods of analgesia and analgesic compositions.

SUMMARY OF THE INVENTION

The present invention provides:

the new use of compounds of Formula II as shown in the accompanying drawings wherein
- $R^1$ is H or Me, preferably H;
- $R^2$ is OH, preferably in alpha conformation;
- $R^3$ is H;
- or $R^2$ and $R^3$, taken together, are O;
- $R^4$ is H or Me, preferably Me and preferably in alpha conformation;
- $R^5$ is H;
- $R^6$ is H;
- or $^5$ and $R^6$, taken together, are O;
- $R^7$ is H or Me, preferably H;
- $R^8$=H,OH,OAc,SH,SAc,Cl,Br,F
including solvates thereof, pharmaceutically acceptable derivatives thereof, prodrugs thereof, tautomers thereof, isomers thereof, and metabolites thereof.

The present invention also provides a method of analgesia comprising administering an effective amount of a compound of Formula II, wherein
- $R^1$ is H or Me, preferably H;
- $R^2$ is OH, preferably in alpha conformation;
- $R^3$ is H;
- or $R^2$ and $R^3$, taken together, are O;
- $R^4$ is H or Me, preferably Me and preferably in alpha conformation;
- $R^5$ is H;
- $R^6$ is H;
- or $R^5$ and $R^6$, taken together, are O;
- $R^7$ is H or Me, preferably H;
- $R^8$=H,OH,OAc,SH,SAc,Cl,Br,F
including solvates thereof, pharmaceutically acceptable derivatives thereof, prodrugs thereof, tautomers thereof, isomers thereof, and metabolites thereof.

The present invention also provides an analgesic composition comprising a compound of Formula II, wherein
- $R^1$ is H or Me, preferably H;
- $R^2$ is OH, preferably in alpha conformation;
- $R^3$ is H;
- or $R^2$ and $^3$, taken together, are O;
- $R^4$ is H or Me, preferably Me and preferably in alpha conformation;
- $R^5$ is H;
- $R^6$ is H;
- or $R^5$ and $R^6$, taken together, are O;
- $R^7$ is H or Me, preferably H;
- $R^8$=H,OH,OAc,SH,SAc,Cl,Br,F
including solvates thereof, pharmaceutically acceptable derivatives thereof, prodrugs thereof, tautomers thereof, isomers thereof, and metabolites thereof.

PREFERRED ASPECTS OF THE INVENTION

The compounds of the invention are related to pregnanedione which is shown in Formula I.

The following Patent Specifications describe some of the compounds and their method of preparation:

British Patent Specification No. 1,317,185 (Application No. 33162/72 filed May 16, 1973) to GLAXO;

German Patent Specification No. 2,255,108 (based on British Application No. 52465/71 filed Nov. 11, 1971) to GLAXO;

U.S. Pat. No. 3,558,608 (granted Jan. 27, 1971, filed Dec. 30, 1968) to SEARLE;

South African Patent Specification 70/03861 (filed Jan. 15, 1971 based on British Application filed Jun. 20, 1969) to GLAXO;

German Patent Specification No. 2,162,554 (filed Jun. 29, 1972, based on British Application No. 60,068/70 filed Dec. 17, 1970) to GLAXO;

French Patent Specification No. 2,118,121 (filed Sep. 1, 1972, based on British Application 60,068/70 filed Dec. 17, 1970) to GLAXO; and German Patent Specification No. 2,162,593 (filed Jul. 6, 1972, based on British Application No. 60,067/70 filed Dec. 17, 1970) to GLAXO.

The whole of the subject matter of those specifications together with items 105627c and 9285v of Chemical Abstracts, Vol. 77, 1972; 64113v, 64114w, 20793n of Chemical Abstract 5, Vol. 75, 1971; 115783f and 66672h of Chemical Abstracts Vol 79, 1973; and 1020345 of Chemical Abstracts Vol 78, 1973 is to be considered included and imported hereinto.

A preferred compound for use is 21-acetoxy-3alpha-hydroxy-5alpha-pregnane-11,20-dione which is of Formula III and which is commonly referred to as alphadolone acetate.

Other compounds which may be suitable for use include: 3alpha-hydroxy-5alpha-pregnan-20-one and 3alpha-hydroxy-5beta-pregnan-20-one which are of Formula IV.

The compounds may be used individually or in mixtures with other compounds of Formula II.

In addition, compounds of Formula II may be used concurrently with other analgesic drugs such as opioids to potentiate or increase the analgesic effects of those drugs.

Suitable opioids for this use include morphine.

The compounds for use in this invention may be provided in free acid form or as a salt. It is preferred that the compounds are provided as either sulphate or methane sulphonate salts.

The compositions of this invention may be prepared for administration by various routes including intravenous, intramuscular, peritoneal and any other convenient route.

However, the applicant has found that effective results are obtained when a compound of Formula II is administered into the intestines particularly intragastrically, and in a particular instance via an oral route.

Accordingly, in a preferred aspect, the present invention provides a composition in a form suitable for oral administration.

That form may include tablet, capsule or lozenge or a liquid form.

It is preferred that the composition contains a surfactant and/or a solubility improver. One solubility improver is water-soluble polyoxyethylated castor oil.

A suitable surfactant is Cremophor EL.

A suitable dosage in a 70 kg human would be about a maximum of 2.00 grams of the compound of Formula II every 6 hours.

BRIEF DESCRIPTION OF THE VIEW OF THE DRAWINGS

EXAMPLES

Example 1

Figure 1:
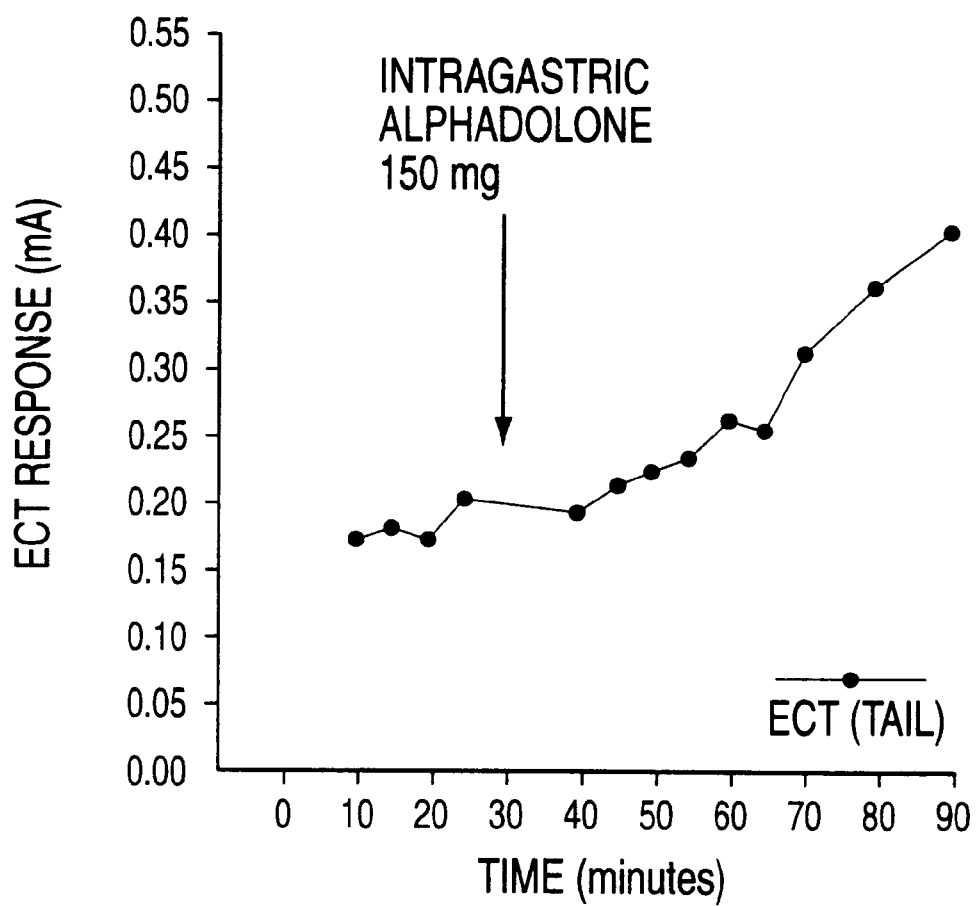
FIG. 1 is a graph showing results obtained.

We performed a pilot experiment on one drug naive male Wistar rat that weighed approximately 200 g. We measured the nociceptive (pain) threshold in the tail using electrical current as the noxious stimulus. We measured the electrical current threshold for pain (ECT) in the tail every five minutes until the readings stabilised. We then gave 150 mg alphadolone acetate suspended in 1% Cremophor EL, 99% saline, intragastrically. Subsequent ECT measurements as shown in FIG. 1 showed a significant rise in tail pain thresholds which lasted a long time after drug administration.

Example 2

We performed a more controlled series of experiments with intragastric alphadolone acetate (150 mg dissolved in 1.0 ml 20% Cremophor EL to 200 g male wistar rats). We measured ECT in the neck and the tail every 5 minutes for 15 minutes before and for some time after drug administration. Five rats received on two successive days at random either alphadolone acetate in Cremophor EL followed by Cremophor alone on the next day or vice versa. These experiments were also performed double blind. By that we mean that, at the time of the experiment the person making the measurements did not know what the rat received, drug plus Cremophor or just Cremophor alone.

Figure 2:
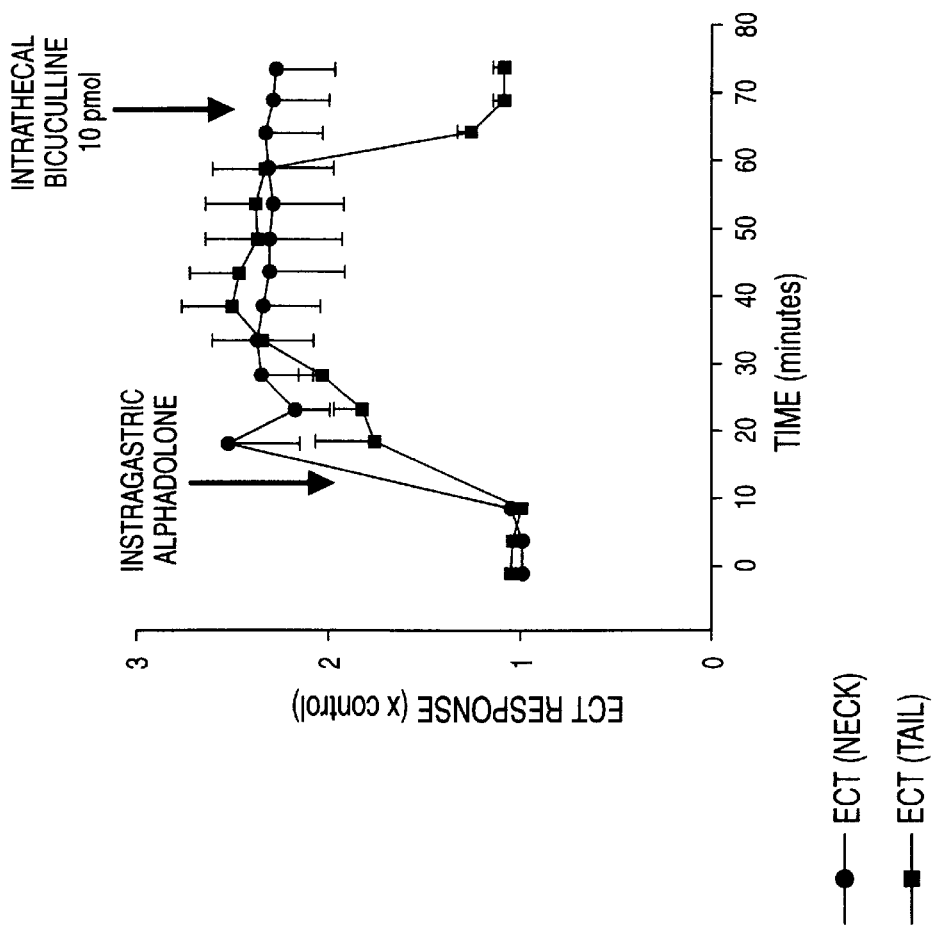
FIG. 2 is a graph showing results obtained.
Figure 2:
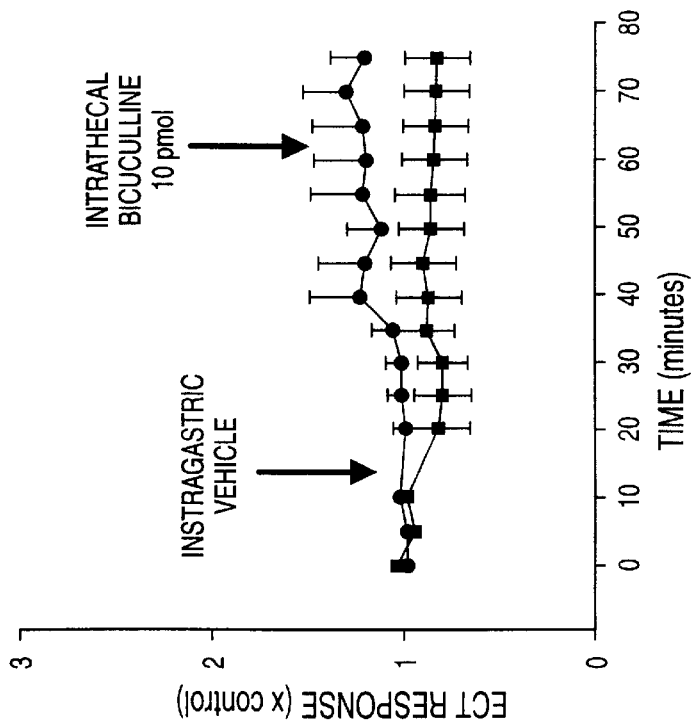
Figure 3:
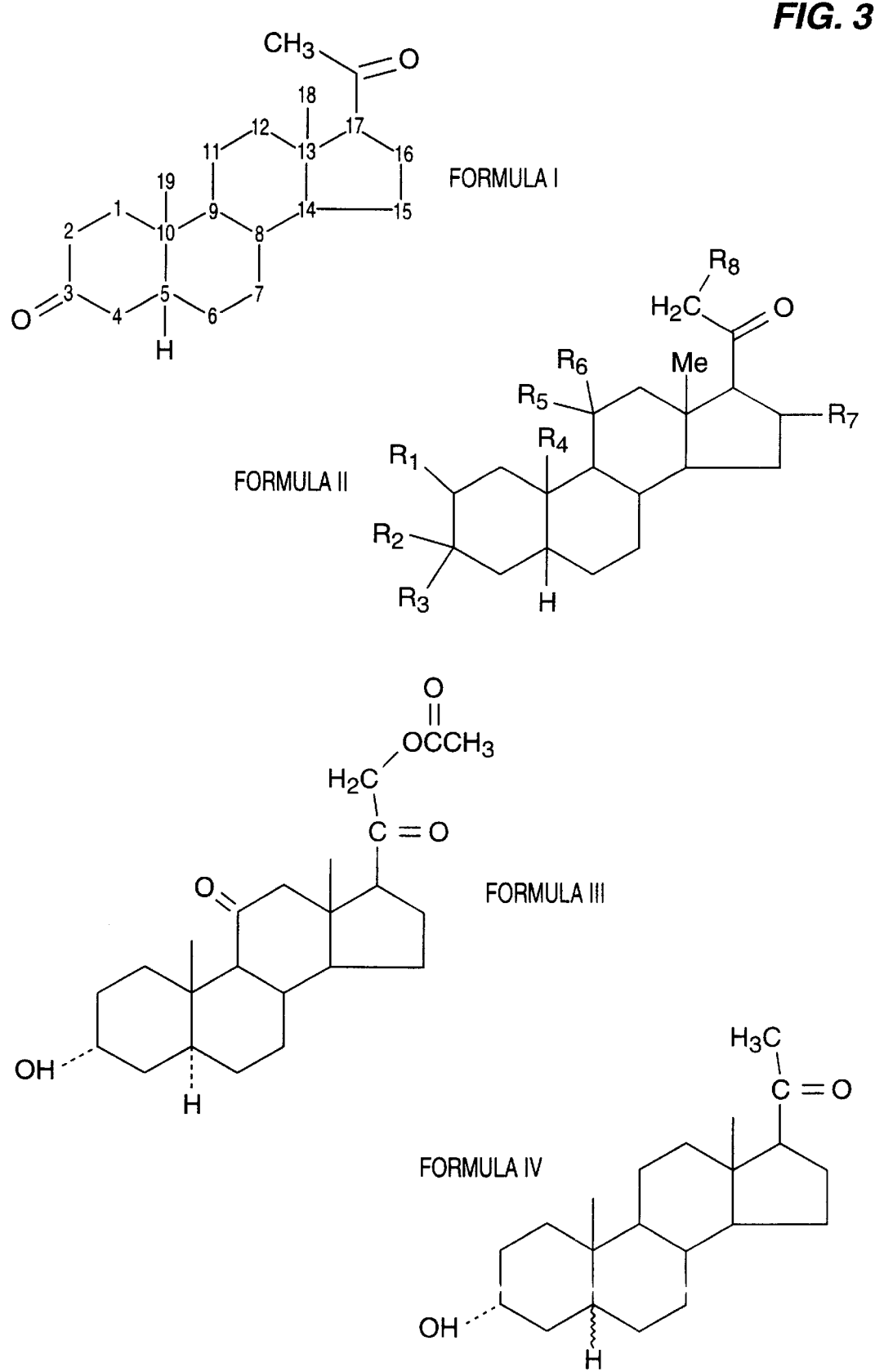
FIG. 3 is formula drawings.

These results are shown in FIG. 2 which is a time response curve showing the mean of the responses in all five rats to the drug with vehicle and vehicle (Cremophor) alone. In all cases alphadolone acetate caused rises in ECT pain thresholds in the neck and tail whereas the vehicle alone had no effect.

In all of these experiments bicuculline 10 pmol was given intrathecally 30 minutes after the intragastric drug or vehicle. By giving bicuculline intrathecally to the lumbrosacral spinal cord we were able to test the theory that the antinociception or pain relief following intragastric alphadolone acetate was due to an action of that drug on spinal cord $GABA_A$ receptors. Bicuculline is a selective $GABA_A$ receptor antagonist. In confining bicuculline to the part of the spinal cord responsible for tail innervation we would expect tail GABA-mediated responses to be reversed but those responsible for neck sensations to be unaffected. That is the result shown in FIG. 2. Thus the conclusion from this is that alphadolone acetate causes analgesia by acting on $GABA_A$ receptors in the spinal cord even when the drug is given into the stomach. The vehicle had no effect the rats were not sedated or exhibited any disturbances in consciousness in any way.

The claims and drawings form part of the disclosure of this specification as does the description, claims, illustrations, photographs and drawings of any associated provisional or parent specification or of any priority document, if any, all of which are imported hereinto as part of the record hereof.

Finally it is to be understood that various alterations, modifications and/or additions may be incorporated into the various constructions and arrangements or parts without departing from the spirit and ambit of the invention.

We claim:

1. A method of analgesia treatment comprising the step of:

administering an effective amount of an analgesic composition comprising morphine and a compound of the formula:

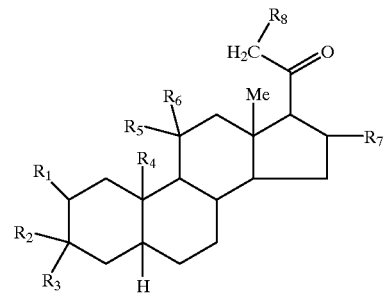

wherein $R^1$ is H or Me, $R^2$ is OH, $R^3$ is H;

or $R^2$ and $R^3$, taken together, are O;

$R^4$ is H or Me, $R^5$ and $R^6$, taken together, are O;

$R^7$ is H or Me, $R^8$=H, OH, OAc, SH, SAc, Cl, Br, F.

2. A method according to claim 1 wherein $R^1$ is H;

$R^2$ is OH in alpha conformation, $R^4$ is Me and $R^7$ is H.

3. A method according to claim 2 wherein $R^4$ is Me in alpha conformation.

4. A method according to claim 1 wherein the compound is alphadolone acetate.

5. An analgesic composition comprising morphine and a compound of the formula:

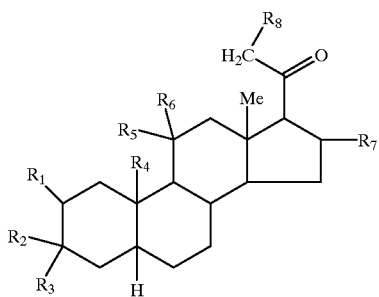
wherein
R¹ is H or Me,
R² is OH,
R³ is H;
or R² and R³, taken together, are O;
R⁴ is H or Me,
R⁵ and R⁶, taken together, are O;
R⁷ is H or Me,
R⁸=H, OH, OAc, SH, SAc, Cl, Br, F.
6. The composition of claim 5 wherein
R¹ is H;
R² is OH in alpha conformation,
R⁴ is Me, and
R⁷ is H.
7. The composition of claim 6 wherein R⁴ is Me in alpha conformation.
8. The composition of claim 5 wherein the compound is alphadolone acetate.
* * * * *